United States Patent [19]

Dempski et al.

[11] 4,173,626

[45] Nov. 6, 1979

[54] SUSTAINED RELEASE INDOMETHACIN

[75] Inventors: Robert E. Dempski, Dresher; Gunvant N. Mehta, Lansdale; Joseph C. Saboe, Norristown, all of Pa.

[73] Assignee: Merck & Co., Inc., Rahway, N.J.

[21] Appl. No.: 968,608

[22] Filed: Dec. 11, 1978

[51] Int. Cl.² .................... A61K 9/22; A61K 9/48
[52] U.S. Cl. ....................... 424/19; 424/20; 424/21; 424/22; 424/37
[58] Field of Search .................... 424/19–22, 424/32–38

[56] References Cited

U.S. PATENT DOCUMENTS

| | | | |
|---|---|---|---|
| 2,702,264 | 2/1955 | Klaui | 424/33 |
| 2,921,883 | 1/1960 | Reese et al. | 424/21 |
| 2,928,770 | 3/1960 | Bardani | 424/21 |
| 3,080,294 | 3/1963 | Shepard | 424/35 |
| 3,081,233 | 3/1963 | Enz et al. | 424/33 |
| 3,247,066 | 4/1966 | Milosovich | 424/35 |
| 3,325,365 | 6/1967 | Hotko et al. | 424/33 |
| 3,400,185 | 9/1968 | Kohnle et al. | 424/33 |
| 3,492,397 | 1/1970 | Peters et al. | 424/35 |
| 3,835,221 | 9/1974 | Fulberth et al. | 424/20 |
| 4,083,949 | 4/1978 | Benedikt | 424/35 |

FOREIGN PATENT DOCUMENTS 694708 8/1940 Fed. Rep. of Germany.
2146174 3/1972 Fed. Rep. of Germany.
6502190 10/1965 Netherlands.

OTHER PUBLICATIONS

Dittgen et al., Pharmazie, 1977, 32(3)185, in Chem. Abstr. 87:11555g (1977).
Garcia, Diss. Abstr. Int. B, 1977, 38(2):602–603 in Chem. Abstr. 87:161724a (1977).
Dittgen et al., Gyogyszereszet, 1976, 20(7):260–262, in Chem. Abstr. 87:189376n (1977).
Kala et al., Pharmazie, 1976 31(11):793–799, in Chem. Abstr. 86:60497c (1977).
Dittgen et al., Gyogyszereszet, 1976, 20(7):260–262, in Chem. Abstr. 85:198123p (1976).
Data Sheet-Indocid®-R-Sustained Release Indomethacin Remington's Pharmaceutical Sciences, 14th Ed. 1970:1699–1714, Mack Pub., Easton, Pa. 18042.
Elanco Products Co., Div. Eli Lilly & Co., "A Great Shape for your Product", P.O. Box 1750, Indianapolis, Ind. 46206.

Primary Examiner—Shep K. Rose
Attorney, Agent, or Firm—William H. Nicholson; Mario A. Monaco

[57] ABSTRACT

A sustained release indomethacin pharmaceutical product is provided that utilizes a pellet formulation encapsulated in a hard gelatin capsule. A portion of the pellets is uncoated for immediate and rapid release of indomethacin for elevating the plasma level. The remainder of the pellets are coated with a polymer to sustain the plasma level. The uncoated and coated pellets may be mixed with non-medicated pellets as a capsule filler.

3 Claims, No Drawings

SUSTAINED RELEASE INDOMETHACIN

BACKGROUND OF THE INVENTION

This invention is concerned with a novel pharmaceutical formulation for the sustained release of indomethacin.

The formulation consists of a capsule comprising uncoated pellets of indomethacin, coated pellets of indomethacin and usually pellets of a non-medicated mixture. By this means there is provided immediately available indomethacin for elevating the plasma level and more slowly released indomethacin for sustaining the plasma level at therapeutic doses over prolonged periods of time.

Indomethacin has been known for years and has been the most successful non-steroidal antiinflammatory agent available for the treatment of inflammatory diseases such as rheumatoid arthritis and osteoarthritis. The use of indomethacin in the traditional pharmaceutical forms such as tablets and capsules has required the ingestion of three or four unit doses per day. Most patients on this therapeutic regimen are elderly and often taking several other tablets or capsules per day for the treatment of other disease states, such as hypertension, depression or the like. Accordingly, it is important for the convenience of the patient and more particularly to ensure compliance by the patient to the particular therapeutic regimen that the number of unit doses per day be kept to a minimum.

In addition to patient convenience and compliance, it is important, particularly in the treatment of rheumatoid arthritis, to maintain a continuous antiinflammatory serum concentration of indomethacin. This is difficult to accomplish with the traditional pharmaceutical forms of indomethacin which are rapidly absorbed providing high serum concentrations and then slowly metabolized to low serum concentrations three or four times a day.

With the present invention there is provided a sustained release form of indomethacin which provides a prolonged antiinflammatory serum level of indomethacin by ingestion of only one unit dose every twelve hours.

SUMMARY OF THE INVENTION

In accordance with the present invention, the sustained release capsule formulation contains uncoated pellets of indomethacin, coated pellets of indomethacin and non-medicated pellets. A loading dose of about 35% of the total indomethacin is supplied by uncoated pellets for immediate release and rapid elevation of plasma levels. A sustaining dose of about 65% of the total indomethacin is supplied by pellets coated with a slowly dissolving polymer. Non-medicated pellets are used as a filler for encapsulation with magnesium stearate as the lubricant.

DETAILED DESCRIPTION OF THE INVENTION

The sustained release pharmaceutical formulation of this invention, as a unit dose, is a capsule containing 25 to 150 mg of indomethacin presented as:

(a) Uncoated pellets comprising pharmaceutical carriers and 5-50 mg of indomethacin;

(b) Coated pellets comprising pharmaceutical carriers and 15-145 mg of indomethacin, wherein the coating is a slow dissolving material.

In the coated and uncoated pellets of indomethacin, the indomethacin constitutes 10 to 35% by weight of the pellets, and is admixed with: a binding agent constituting 20-40% by weight of the pellet, such as a sugar, for example sucrose, lactose, sorbitol, mannitol, invert sugar, dextrose, fructose or the like, especially sucrose; a second binding agent, constituting about 3 to about 15% by weight of the pellet, such as hydroxypropylmethylcellulose, hydroxypropylethylcellulose, methylcellulose, sodium alginate, sodium carboxymethylcellulose, polyvinyl alcohol, polyvinylpyrrolidone, starch paste, gum acacia, gelatin, or the like; a disintegrating agent constituting about 3–15% by weight of the pellet, such as corn starch, guar gum, gum tragacanth, agar, sodium starch glycolate, or the like; and a diluent constituting about 10–30% by weight of the pellet, such as microcrystalline cellulose, alginic acid, lactose, maltose, dextrose or the like.

The coated pellets are coated with a slow dissolving material, such as polyvinylacetate, methacrylic acid esters, ethylcellulose, polyvinyl alcohol, hydroxypropylmethylcellulosephthalate, cellulose acetate, cellulose acetate phthalate, or the like.

In the unit dosage of this invention it is convenient but not necessary to include unmedicated pellets to achieve the correct adjusted fill volume for the capsule. It can be any art recognized placebo mixture but for ease of encapsulation it is desirable to have the placebo in a particle size comparable with the coated and uncoated pellets previously described. The non-medicated portion is not a critical part of the novel unit dose pharmaceutical formulation of this invention. A typical non-medicated pellet is described in the Examples that follow.

For ease of encapsulation it is preferred to incorporate a lubricant such as talc, stearic acid or magnesium stearate, comprising from about 0.1 to about 1.0% by weight of the capsule contents.

(A) Uncoated Indomethacin Pellets

The ingredients, previously described are blended, milled and remixed according to acceptable pharmaceutical manufacturing practices. The powder mixture is then granulated with purified water and extruded as rods approximately 1 mm in diameter. The granulated rods placed in a pelletizer, or spheronizer and the resulting pellets are dried. The dried pellets are sized using standard sieves, retaining these pellets between about 500 microns and 1500 microns in size. A preferred size range is about 1190 microns (#16 screen) to about 590 microns (#30 screen).

(B) Coated Indomethacin Pellets

Uncoated indomethacin pellets are coated with a slow dissolving coating agent in accordance with accepted pharmaceutical manufacturing procedures, and dried. The dried pellets are sized as described for the uncoated pellets.

(C) Non-medicated Pellets

The ingredients previously described less the indomethacin are blended, milled and remixed, granulated with purified water and extruded into rods of about 1 mm diameter. The rods are placed in a spheronizer or pelletizer and the resulting pellets are dried. The dried pellets are sized as previously described and retained in an air tight container. These pellets may also contain a pharmaceutically acceptable coloring agent such as FD & C Blue No. 2, FD & C Red No. 3, or the like.

The required quantities of uncoated indomethacin pellets and coated indomethacin pellets are selected to achieve the desired content of indomethacin, and to obtain the desired release pattern for the finished product. Non-medicated pellets are added as required to achieve the correct adjusted fill volume for the capsule. These materials are blended with a lubricating agent such as magnesium stearate and encapsulated.

Examples of typical capsules are shown in Tables I-IV.

TABLE I
INDOMETHACIN SUSTAINED RELEASE CAPSULE COMPOSITION, 75 MG.

| Per Capsule (mg) | Capsule Composition | Percentage |
|---|---|---|
| 80 | Indomethacin Uncoated Pellets | |
| That contains: | | |
| 25 | Indomethacin | 31.25 |
| 28 | Confectioner's Sugar | 35.00 |
| 5 | Hydroxypropylmethyl-cellulose | 6.25 |
| 7 | Starch, Corn USP | 8.75 |
| 15 | Microcrystalline Cellulose NF | 18.75 |
| 165 | Indomethacin Coated Pellets | |
| That Contains: | | |
| 50 | Indomethacin | 30.30 |
| 56 | Confectioner's Sugar | 33.94 |
| 10 | Hydroxypropylmethyl-cellulose | 6.06 |
| 14 | Starch, Corn USP | 8.48 |
| 30 | Microcrystalline Cellulose NF | 18.18 |
| 5 | Polyvinylacetate | 3.04 |
| 50 | White Placebo Pellets | |
| That Contains: | | |
| 25 | Confectioner's Sugar | 50.00 |
| 5 | Hydroxypropylmethyl-cellulose | 10.00 |
| 6 | Starch, Corn USP | 12.00 |
| 14 | Microcrystalline Cellulose NF | 28.00 |
| 0.5 | Magnesium Stearate USP | |
| 295.5 | TOTAL NET WEIGHT | |

TABLE II
INDOMETHACIN SUSTAINED RELEASE CAPSULE COMPOSITION, 25 MG.
Detailed Composition

| Ingredient | mg/Capsule |
|---|---|
| Uncoated Indomethacin Pellets | 60.00 |
| which contain: | |
| Indomethacin | 13.9% |
| Sugar, Powdered with 3% Starch | 43.9 |
| Hydroxypropylmethylcellulose NF 50 cps 60 HG | 8.3 |
| Microcrystalline Cellulose NF | 23.3 |
| Water, Purified USP | — |
| Starch, USP, Corn | 10.6 |
| Coated Indomethacin Pellets | 55.00 |
| which contain: | |
| Indomethacin, | 30.3% |
| Sugar, Powdered with 3% Starch | 33.9 |
| Hydroxypropylmethylcellulose NF 50 cps 60 HG | 6.1 |
| Starch, USP, Corn | 8.5 |
| Microcrystalline Cellulose NF | 18.2 |
| Cellulose Acetate | 5.0 |
| Water, Purified USP | — |
| SD3A Alcohol, 95% | — |
| White Non-Medicated Pellets | 69.75 |
| which contain: | |
| Sugar, Powdered with 3% Starch | 51.0% |
| Hydroxypropylmethylcellulose NF 50 cps 60 HG | 10.0 |
| Starch, USP, Corn | 12.0 |
| Microcrystalline Cellulose NF | 27.0 |
| Water, Purified USP | — |
| Magnesium Stearate USP | 0.25 |
| TOTAL CAPSULE NET WEIGHT | 185.0 |

TABLE III
INDOMETHACIN SUSTAINED RELEASE CAPSULE COMPOSITION, 150 MG.
Detailed Composition

| Ingredient | mg/Capsule |
|---|---|
| Uncoated Indomethacin Pellets | 110.0 |
| which contain: | |
| Indomethacin | 31.25% |
| Sugar, Powdered with 3% Starch | 35.0 |
| Hydroxypropylmethylcellulose NF 50 cps 60 HG | 6.25 |
| Starch, USP, Corn | 8.75 |
| Microcrystalline Cellulose NF | 18.75 |
| Water, Purified USP | — |
| Coated Indomethacin Pellets | 330.0 |
| which contain: | |
| Indomethacin | 30.3% |
| Sugar, Powdered with 3% Starch | 34.0 |
| Hydroxypropylmethylcellulose NF 50 cps 60 HG | 6.1 |
| Starch, USP, Corn | 8.5 |
| Microcrystalline Cellulose NF | 16.1 |
| Polyvinylacetate | 5% |
| Water, Purified USP | — |
| SD3A Alcohol, 95% | — |
| Non-Medicated Pellets | 99.0 |
| which contain: | |
| Sugar, Powdered with 3% Starch | 51.0% |
| Hydroxypropylmethylcellulose NF 50 cps 60 HG | 10.0 |
| Starch, USP, Corn | 12.0 |
| Microcrystalline Cellulose NF | 27.0 |
| FD & C Blue #2, 92% Pure Dye | 0.05 |
| Water, Purified USP | — |
| Magnesium Stearate USP | 1.0 |
| TOTAL CAPSULE NET WEIGHT | 590.0 |

TABLE IV
INDOMETHACIN RELEASE CAPSULE COMPOSITION, 75 MG.
Detailed Composition

| Ingredient | mg/Capsule | |
|---|---|---|
| Uncoated Indomethacin Pellets | 80.0 | |
| which contain: | | |
| Indomethacin | 31.25% | 31.25% |
| Sugar, Powdered with 3% Starch | 28.00 | 38.00 |
| Hydroxypropylmethylcellulose NF 50 cps 60 HG | 8.00 | 4.25 |
| Starch, USP Corn | 7.00 | 10.75 |
| Microcrystalline Cellulose NF | 25.75 | 15.75 |
| Water, Purified USP | — | — |
| Coated Indomethacin Pellets | 165.0 | |

TABLE IV-continued
INDOMETHACIN RELEASE CAPSULE COMPOSITION, 75 MG.

| Ingredient | Detailed Composition | mg/Capsule |
|---|---|---|
| which contain: | | |
| Indomethacin | 30.3% | 30.3% |
| Sugar, Powdered with 3% Starch | 27.0 | 25.0 |
| Hydroxypropylmethylcellulose NF 50 cps 60 HG | 10.0 | 10.0 |
| Starch, USP Corn | 5 | 7.5 |
| Microcrystalline Cellulose NF | 21.7 | 22.2 |
| Polyvinylacetate | 6% | — |
| Water, Purified USP | — | — |
| SD3A Alcohol, 95% | — | — |
| Ethyl Cellulose | — | 5% |
| Non-Medicated Pellets | | 49.5 |
| which contain: | | |
| Sugar, Powdered with 3% Starch | 45% | 54% |
| Hydroxypropylmethylcellulose NF 50 cps 60 HG | 8 | 9% |
| Starch USP Corn | 14 | 11% |
| Microcrystalline Cellulose NF | 33% | 26% |
| FD & C Blue #2, 92% Pure Dye | 0.15% | 0.3% |
| Water, Purified USP | — | — |
| Magnesium Stearate USP | | 0.5 |
| TOTAL CAPSULE NET WEIGHT | | 295.0 mg |

What is claimed is:

1. A sustained release pharmaceutical formulation in capsule unit dosage form that provides prolonged plasma levels of indomethacin and is clinically effective, containing 25 to 150 mg of 500 to 1500 micron size pellets of indomethacin, in the form of:
   (A) Uncoated pellets comprising pharmaceutical carriers and 5–50 mg of indomethacin for immediate release of about 35% of the total indomethacin, and rapid elevation of plasma levels; and
   (B) Coated pellets comprising pharmaceutical carriers and 15–145 mg of indomethacin as a sustaining dose of about 65% of the total indomethacin wherein the coating consists of polyvinyl acetate as a slow dissolving material.

2. The pharmaceutical formulation of claim 1, wherein the unit dosage form also includes non-medicated pellets to achieve the correct adjusted fill volume for the capsule.

3. The pharmaceutical formulation of claim 1, wherein component (A) is pellets comprising 10–35% by weight indomethacin; 20–40% by weight confectioner's sugar; 3–15% by weight of hydroxypropylmethylcellulose; 3–15% by weight corn starch; and 15–25% by weight microcrystalline cellulose; and component (B) is component (A) pellets coated with said slow dissolving material.

* * * * *